US009915719B2

United States Patent
Popescu (10) Patent No.: US 9,915,719 B2
(45) Date of Patent: Mar. 13, 2018

(54) MAGNETIC RESONANCE IMAGING WITH RANDOMLY DISTRIBUTED RECORDING OF RAW DATA

(71) Applicant: Siemens Aktiengesellschaft, Munich (DE)

(72) Inventor: Stefan Popescu, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 475 days.

(21) Appl. No.: 14/719,673

(22) Filed: May 22, 2015

(65) Prior Publication Data
US 2015/0338491 A1 Nov. 26, 2015

(30) Foreign Application Priority Data
May 22, 2014 (DE) .................. 10 2014 209 753

(51) Int. Cl.
| | | |
|---|---|---|
| *G01V 3/00* | (2006.01) | |
| *G01R 33/565* | (2006.01) | |
| *A61B 5/055* | (2006.01) | |
| *A61B 5/00* | (2006.01) | |
| *G01R 33/48* | (2006.01) | |
| *G01R 33/561* | (2006.01) | |
| *G01R 33/563* | (2006.01) | |

(52) U.S. Cl.
CPC ........ *G01R 33/56509* (2013.01); *A61B 5/055* (2013.01); *A61B 5/7289* (2013.01); *G01R 33/4824* (2013.01); *G01R 33/561* (2013.01); *G01R 33/563* (2013.01); *G01R 33/5617* (2013.01); *G01R 33/56366* (2013.01)

(58) Field of Classification Search
CPC .......... G01R 33/56509; G01R 33/4824; A61B 5/055; A61B 5/7289
See application file for complete search history.

(56) References Cited

U.S. PATENT DOCUMENTS

| | | |
|---|---|---|
| 2012/0008844 A1 | 1/2012 | Bilgin et al. |
| 2012/0083687 A1* | 4/2012 | Parker .................... A61B 5/024 600/419 |
| 2013/0006098 A1 | 1/2013 | Schmitt |
| | | (Continued) |

OTHER PUBLICATIONS

Haldar et al., Compressed-Sensing MRI With Random Encoding, IEEE Transactions on Medical Imaging, vol. 30, No. 4, Apr. 2011.*
(Continued)

*Primary Examiner* — Daniel Miller
(74) *Attorney, Agent, or Firm* — Schiff Hardin LLP (57) ABSTRACT

In a method and apparatus for recording magnetic resonance (MR) signals from an examination object, raw data space is filled with MR signals in raw data lines. Movement information of the examination object is detected during recording of the MR signals and the movement information is grouped into different movement phases of the examination object. A temporally randomly distributed sequence of the recording of the raw data lines is determined, with which at least one predetermined portion of the raw data space is filled MR signals. The MR signals are acquired in the determined temporally randomly distributed sequence of the raw data lines in the predetermined portion. Each recorded raw data line is allocated to one of the movement phases of the examination object.

12 Claims, 5 Drawing Sheets

(56) References Cited

U.S. PATENT DOCUMENTS

2013/0310678 A1   11/2013   Balbi et al.
2014/0009156 A1   1/2014    Doneva et al.
2014/0035582 A1   2/2014    Boernert et al.
2014/0301622 A1   10/2014   Forman
2015/0073263 A1   3/2015    Gdaniec et al.

OTHER PUBLICATIONS

Gdaniec, et al.: "Novel Sampling Strategy for Abdominal Imaging with Incomplete Breathholds", in: Proc.Intl.Soc.Mag.Reson.Med. 20(2012), vol. 20, pp. 600; (2012).
Moghari et al."Compressed-Sensing Motion Compensation (CosMo). A Joint Prospective-Retrospective Respiratory Navigator for Coronary MRI", Magnetic Resonance in Medicine, No. 66, pp. 1674-1681 (2011).

* cited by examiner

MAGNETIC RESONANCE IMAGING WITH RANDOMLY DISTRIBUTED RECORDING OF RAW DATA

BACKGROUND OF THE INVENTION

Field of the Invention

The present invention concerns a method for recording magnetic resonance (MR) signals from an examination object in an MR system, wherein at least part of the examination object moves during the data acquisition. The invention also concerns an MR system for implementing such a method.

Description of the Prior Art

If the examination object moves during recording (acquisition) of the MR signals, this leads to an incorrect registering of the measured MR data and to image artifacts, also called ghosting. The movement of the examination object, e.g. an examination person, usually occurs due to breathing or due to the movement of the heart or due to other undesirable movements such as a tremor in elderly or ill patients. Most movement in an examination object is periodic, wherein each cycle of movement can constitute a problem, particularly in the case of long recording times. One possibility for imaging moving examination objects is known as the single-shot technique, in which the raw data domain (k-space) is filled completely after radiation of an RF pulse and in which recording of the data is quick enough to freeze the movement. A further recording possibility is the segmented recording technique in which the data acquisition is divided into multiple movement phases and MR data are recorded only in comparable movement phases. The first possibility mentioned above limits the measurement time, and the second possibility increases the complexity of the measurement and is not effective since MR signals are recorded only in certain movement phases.

There is also the possibility of detecting the movement of the examination object and, as in the segmented recording technique, of using only the movement phases in which a slight movement occurs, but this lengthens the recording time, and this in turn increases the probability of the examination person moving. A method for recording MR signals is therefore needed in which MR data are recorded in all movement phases of a moving examination object.

One possibility for correcting movement artifacts is to fill raw data space with raw data lines such that the movement occurs when the peripheral raw data are recorded, i.e. the outer k-space region is filled, with the MR data falsified by movement then being replaced. However, this leads to a reduction in the spatial resolution due to missing portions of raw data.

Compressed Sensing Technology also is known, in which severe under-sampling of raw data spaces occurs and additional information e.g. about the recorded MR image, is used. The raw data disrupted by movement are replaced by calculated portions of raw data. Mehdi et al describe in "Compressed Sensing Motion Compensation (CosMo): A Joint Prospective-Retrospective Respiratory Navigator for Coronary MRI", *Magnetic Resonance in Medicine* 66:1674-1681 (2011) the use of a method of this kind in which raw data falsified by movement are replaced with the use of Compressed Sensing Technology. A prerequisite for this is a random distribution of the remaining non-rejected MR raw data in the MR raw data space.

WO 2013/140276 A1 describes a reconstruction method in which MR raw data are recorded, wherein the density of the recorded raw data is increased incrementally until the examination person starts to breathe.

To summarize, all of the above-described methods have certain drawbacks.

SUMMARY OF THE INVENTION

An object of the present invention is to at least partially avoid these drawbacks and to provide a method in which moving examination objects produce MR images that have few or no movement artifacts. MR data should preferably be recorded during the different movement phases and be used for image reconstruction.

According to one aspect of the invention, a method for recording MR signals from an examination object in an MR system is provided in which raw data space is filled with MR signals during recording of the MR signals in raw data lines. In this method, movement information of the examination object is detected during recording of the MR signals and the movement information is grouped into different movement phases of the examination object. A temporally randomly distributed sequence for the recording of the raw data lines, with which at least one predetermined portion of the raw data space is filled with MR signals, is also determined. The MR signals are then recorded in the determined temporally randomly distributed sequence of the raw data lines in the predetermined portion of the raw data space, and each recorded raw data line is allocated to a movement phase of the examination object.

The requirements that are necessary for reconstructing portions of the raw data space using Compressed Sensing Technology are better met by the resulting randomly distributed or randomized sequence of the raw data lines in the raw data space, which form part of the same movement phase. There is a statistical randomly distributed data volume in the raw data space as a result of the above-described method. In particular the arrangement of the raw data, in which there was a movement and in which there was no movement, is randomly distributed in the raw data space. The movement is randomly distributed regardless of whether respectively adjacent raw data lines belong to the same or different movement phases. Because in the prior art successive adjacent raw data lines are read, spatially adjacent raw data lines are always affected by the same movement. MR images with slight movement artifacts can be reconstructed with this requirement.

Recorded raw data lines are preferably identified in which the examination object is in a movement rest phase in which there are the most raw data lines per movement phase. A reference image can be calculated from the movement rest phase with the use of these identified raw data lines. A further MR image is also calculated in at least one other movement phase. The further MR image is then calculated using the raw data lines which were recorded in the at least one other movement phase and the reference image, with the reference image being used by way of example in the PICCS method (Prior Image Constraint Compressed Sensing) to determine the missing raw data lines in the other movement phase with the use of Compressed Sensing Technology. Since the examination object remains longest in the movement phase in which the most raw data lines were recorded, this phase is also called a movement rest phase.

The further MR image can be determined, for example, with the use of an iterative reconstruction method in this connection, in which a cost function is minimized.

The temporally randomly distributed recording of the raw data lines can occur in a region of the raw data space outside of a predetermined central region of the raw data space. The central region of the raw data space can be recorded, for example, in the movement rest phase, it being possible to record the raw data lines outside of this predetermined central region during all movement phases.

If the raw data space is a two-dimensional Cartesian raw data space that is filled with MR signals entered into different raw data lines a phase encoding direction, it is temporally randomly chosen when a raw data line is filled with MR signals in the phase encoding direction. The raw data lines in which a pronounced movement occurs are therefore randomly distributed spatially in the phase encoding direction. The raw data space can also be a three-dimensional raw data space, with a temporally randomly distributed sequence of the recording of the raw data lines being determined in a first direction of the three-dimensional raw data space and in a second direction perpendicular thereto a temporally randomly distributed sequence of the recording of the raw data lines being determined. If the raw data lines run parallel to the third spatial direction, then it is chosen in a randomly distributed manner when which raw data lines in the two other spatial directions perpendicular thereto are recorded.

Radial recording of the raw data space is also possible with radial raw data lines that run through the center of the raw data space. The read sequence of the radial raw data lines can also be chosen so as to be temporally randomly distributed. This means that the individual raw data lines or spokes have an angle, relative to an arbitrarily chosen reference data line, with the sequence of angles in the sequence of measured raw data lines being temporally randomly distributed. This means that raw data lines that are adjacent are not recorded, and instead raw data lines are recorded that are temporally randomly distributed one after the other over the circle.

The invention also concerns a magnetic resonance apparatus for implementing the method described above.

DESCRIPTION OF THE PREFERRED EMBODIMENTS

Figure 1:
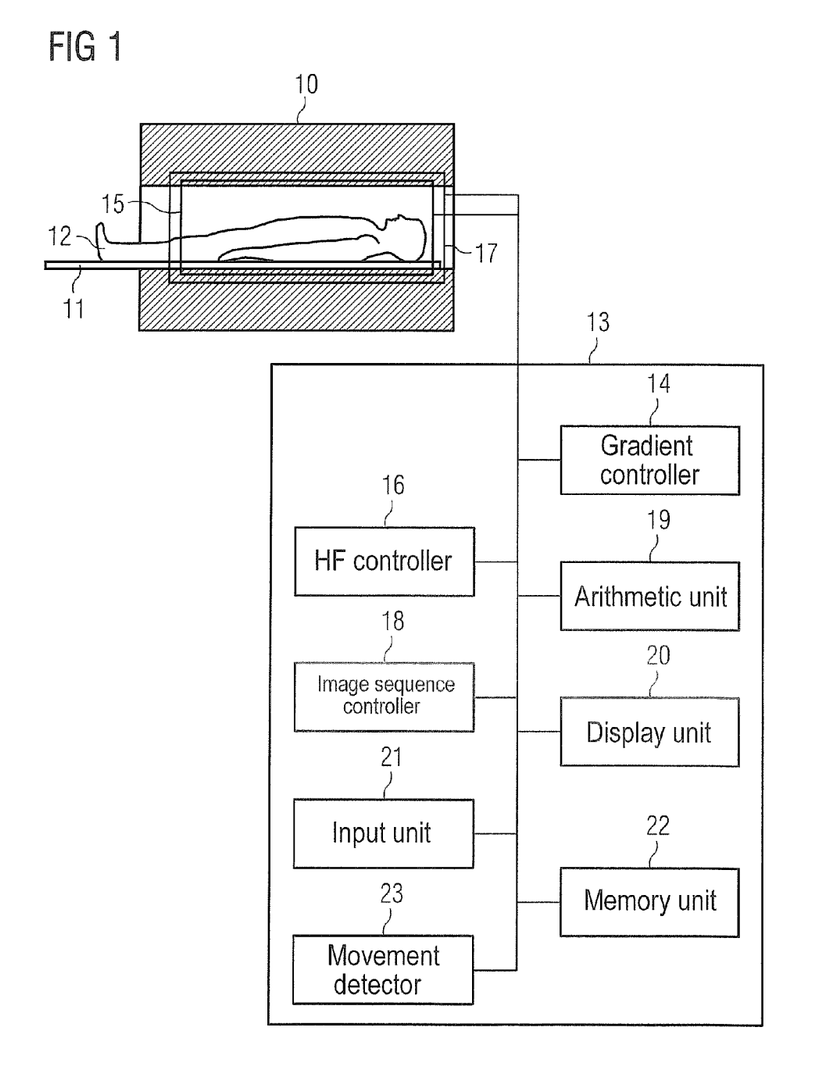
FIG. 1 schematically illustrates an MR system with which inventive MR images of moving examination objects are generated, in which the movement artifacts are minimized.

FIG. 1 schematically shows a magnetic resonance apparatus, with which inventive MR images of an examination object can be generated, which object executes a movement, preferably a cyclical movement. The magnetic resonance apparatus has a scanner with magnet 10 that generates a polarization field B0, with an examination person 12, as the examination object, arranged on a bed 11 that is moved into the center of the magnet 10 in order to record spatially encoded magnetic resonance signals of the examination object from at least a portion of the examination object. By radiating radio-frequency pulse sequences and switching magnetic field gradients nuclear spins with the magnetization produced by the polarization field B0 are deflected from the state of equilibrium and the resulting signal echoes are detected as MR signals by receiving coils (not shown). The magnetic resonance apparatus also has a central control computer 13 that is configured to operate the MR scanner. The central control computer 13 has a gradient controller 14 for controlling and switching magnetic field gradients that are generated by one or more gradient coils 15. A radio-frequency (RF) controller 16 is provided for controlling and radiating the RF pulses for producing the magnetization with the use of an MR coil 17. The coil can be a transmitting and receiving coil and can be designed as a body coil or as a local coil or a combination of the two. After selection of an imaging sequence, an image sequence controller 18 controls the sequence of the magnetic field gradients and the RF pulses and therefore also controls the RF controller 16 and the gradient controller 14. The MR signals detected by the coil are converted in an arithmetic processor 19 into an MR image and can be displayed on a display unit 20. Inputs for the MR system can be made via an input interface 21. Different imaging sequences and sequences of imaging sequences are used to acquire MR data from specific regions of the body can be stored in and accessed from a memory unit 22.

Program codes or programs may also be stored in the memory unit 22, which, when run in the control computer 13, are required for operation of the MR system. Those skilled in the art know how MR signals can be produced by a sequence of magnetic field gradients and RF pulses, so this need not be explained in more detail herein. A movement detector 23 detects movement of at least a portion of the examination person and groups the movement into different movement phases. It is also possible for the grouping into different movement phases to occur in the arithmetic processor 19, which analyses the data of the detector 23. The movement detector can be, for example, a breathing belt, an ECG or a camera that detects the movement of the object and possibly also analyzes the movement.

It will be explained in more detail below how the imaging sequence controller 18 inventively controls the temporal sequence of the recorded MR signals such that a randomized distribution of the raw data that belong to the same movement phase is possible in the raw data space (k-space).

The raw data space is filled with MR signals such that a random acquisition sequence of the raw data lines is implemented. As an example, a randomization can occur over time if the instant at which a raw data line is read is randomly chosen. There is therefore also a spatial random distribution of the raw data lines in which there is a movement position or amplitude. The raw data lines, which belong to one movement phase, are also randomly distributed spatially in the raw data space. As will be explained in detail below, the inventive recording method can be used in the two-dimensional or three-dimensional acquisition of raw data.

Figure 2:
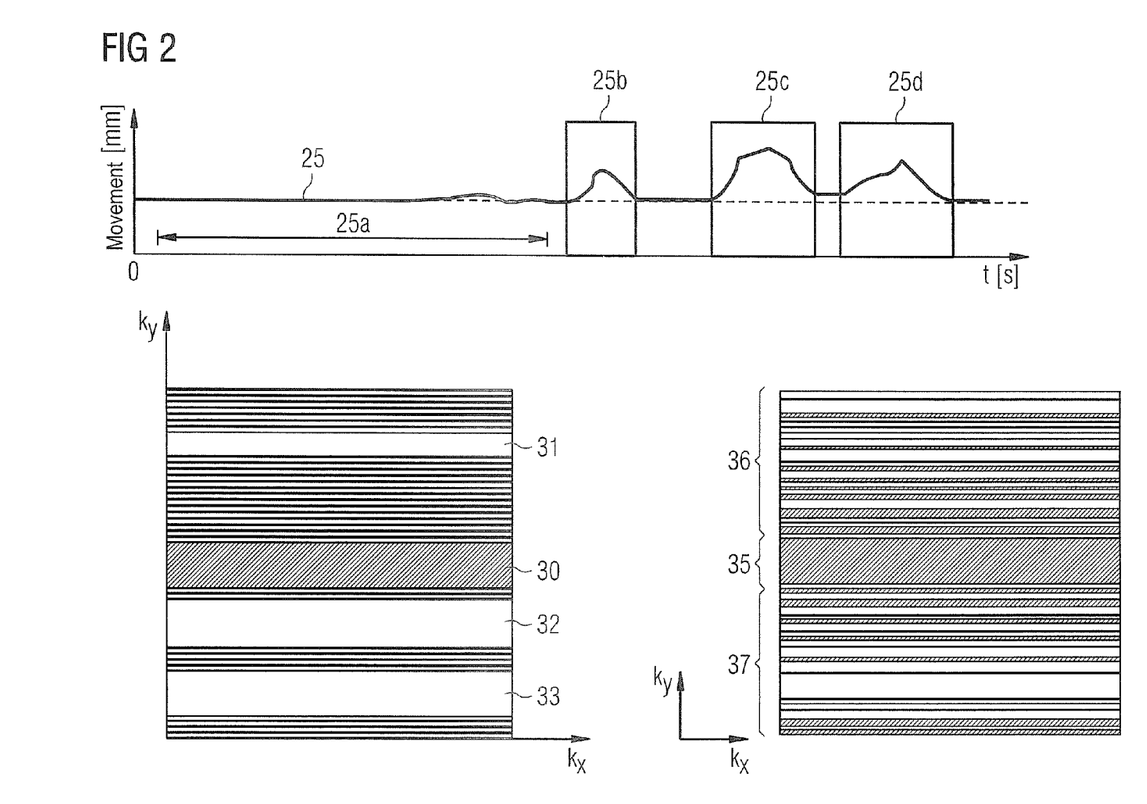
FIG. 2 schematically shows the movement sequence of an examination object and the associated filling of the raw data space with raw data lines according to the prior art, as well as according to the invention.

FIG. 2 shows how a random or statistical distribution of the recorded MR signals relative to a movement phase is achieved in a two-dimensional Cartesian recording of the raw data space. The examination object chosen in the examination person, such as by way of example part of the abdomen, can execute a movement, as is shown by course over time 25 in the upper section of FIG. 2. This may be the respiratory movement, for example, wherein in a first section 25a the examined region of the body was almost completely at rest, such as because the examination person held his or her breath. During the time frames 25b, 25c and 25d there was a movement, here a respiratory movement, of the examined region. The left side of FIG. 2 shows how in a two-dimensional Cartesian case the raw data space is filled with raw data according to the prior art. A central region, as an example, of the raw data space 30 can be recorded during the time frame 25a, wherein the k-space or raw data lines outside of the central region 30 are recorded consecutively. The outer raw data regions are then recorded in such a way that the raw data region 31 is recorded during the time frame 25b, the raw data region 32 during the time frame 25c, and the raw data region 33 during the time frame 25d. This means, as shown on the left of FIG. 2, that the raw data lines, which are affected by the movement, are located in a respectively continuous k-space. If there is then an attempt to calculate the raw data regions 31, 32 and 33, which constitutes gaps, for example using Compressed Sensing Technology, i.e. to fill the gaps, blurry images result since the necessary random distribution of missing raw data in the raw data space is absent.

The right lower region of FIG. 2 shows the recording of MR data according to one embodiment of the invention. A central raw data region 35, for example, can again be recorded during a time frame in which it is known that the movement of the examination region is minimal, or in which as many raw data lines as possible belong to one movement phase. In a region of the raw data space outside of the predetermined central region 35 the phase encoding values ky are then temporally randomly, chosen so that it is randomly chosen when each k-space line in the raw data regions 36 and 37 is read. In the raw data image shown on the right in FIG. 2 the regions are again shown, analogously to the left raw data image, as regions without raw data lines in which a movement has taken place, such as a movement during the time frames 25b-d. As may be seen in the right part of FIG. 2, here the regions with missing raw data lines are not distributed so as to be continuous as on the left in FIG. 2, but indiscriminately over ky. In the right part of FIG. 2 the raw data lines corrupted by movement are randomly distributed over the outer raw data regions 36 and 37. This spatial random distribution of the raw data is particularly suitable for Compressed Sensing Reconstruction Technology and to a large extent minimizes the movement artifacts that consequently arise. If the central raw data region 35 is read (filled) in a movement rest phase in which a large number of raw data lines can be recorded, then this allows a good contrast, by way of example in the case of T2-weighted multi-spin echo sequence or spin echo epo sequences or perfusion studies.

Figure 3:
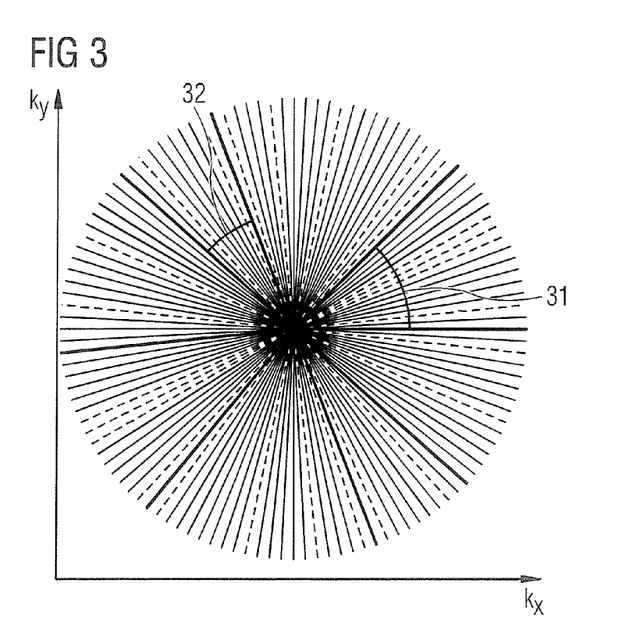
FIG. 3 schematically shows aspects of the invention with the application of the radial recording methods.

FIG. 3 shows the inventive method in the case of a two-dimensional radial recording technique. The raw data lines designed here as spokes are not measured in a sequential sequence in such a way that an incremental change in the angle leads to adjacent spokes always being successively read over the whole circle. In the case of the spokes shown in FIG. 3 the sequence over time of the individual spokes is instead randomly chosen. This leads to a pattern in which the raw data lines (shown in broken lines), in which the examination object is moving, are randomly distributed over the disk. If there is then a time frame with movement in the movement phase, such as by way of example one of the phases 25b-d of FIG. 2, this means that the raw data lines affected by movement errors have a random distribution in k-space. If the raw data lines, which are affected by movement, are replaced with the use of Compressed Sensing Technology then this leads to an MR image with much fewer artifacts or no artifacts compared to the case where segments of a circle, such as the segment 31 or 32 with the associated raw data lines have to be reconstructed completely using Compressed Sensing Technology if the spokes in the circle are read consecutively, as is conventional in the prior art.

Figure 4:
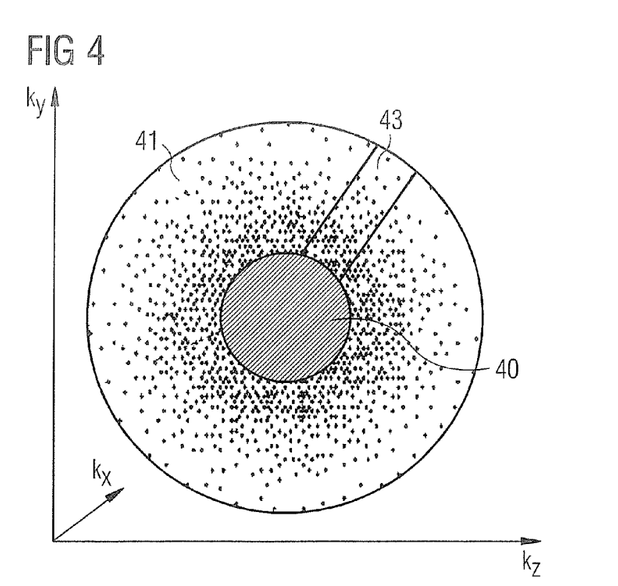
FIG. 4 schematically shows aspects of the invention in the recording of MR signals in a three-dimensional Cartesian raw data space.

An embodiment is shown in connection with FIG. 4 in which a three-dimensional image is acquired with individual raw data lines which run into the drawing plane, the read direction is along kx, so that a cylindrical raw data space results with the axis in the kx direction. In this embodiment the central raw data region is again filled with MR signals during the rest phase 25a shown in FIG. 2. The raw data region outside of the center with the reference numeral 41 is then read such that the individual dots shown in FIG. 4, which constitute a raw data line in the kx direction, are read in a temporally randomly distributed manner. The choice is made in a temporally randomly distributed manner in the kz direction and in the ky direction perpendicular thereto. This means that it is chosen in a temporally randomly distributed manner when the raw data line shown as a dot is read with a specific ky and a specific kz value. This in turn leads to a spatially random distribution of the raw data lines in the three-dimensional space in which the recorded MR signals are adversely affected by movement. If the three-dimensional raw data space had been read using a method of the prior art, segments such as the segment 43 by way of example would be filled as a whole with raw data lines which are affected by the movement. This would mean that all raw data lines in segment 43 would have to be replaced, and this constitutes a continuous block of raw data lines. The reconstruction of continuous blocks of this kind, such as block 43, can be prevented according to the invention, however, since the raw data lines to be reconstructed are randomly distributed over the raw data space.

Figure 5:
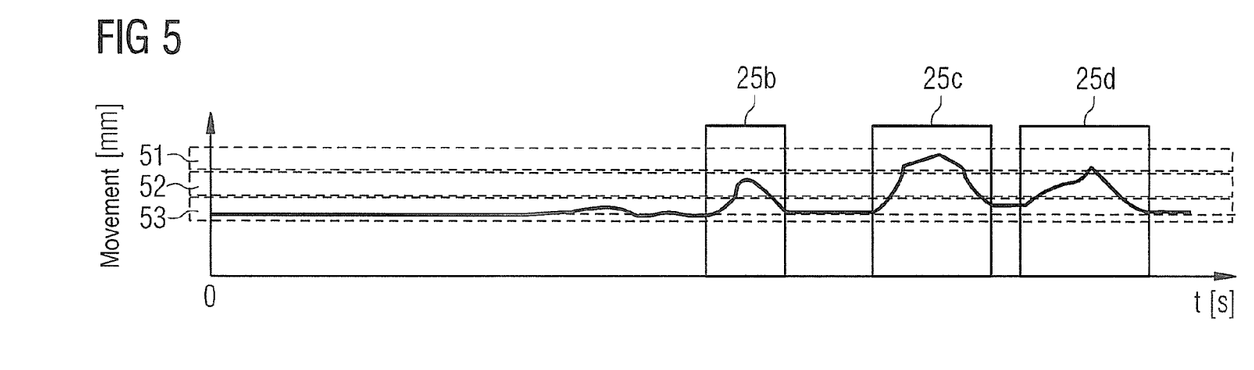
FIG. 5 schematically shows the calculation of MR images in movement phases in which there is movement, taking into account prior knowledge of an MR image which was recorded during a rest phase.

In the previously described method the raw data lines, in which a movement occurred which is greater than a limit value, are discarded and can be calculated by way of example with the aid of Compressed Sensing Technology. In the exemplary embodiment shown below in FIG. 5 all raw data or k-space lines can be used for image reconstruction, even the raw data lines which were recorded during movement of the examination object. As shown in FIG. 5, different movement phases 51, 52 or 53 are identified in this embodiment. The movement phase 53 is, as an example, the movement phase that is to be categorized as the movement rest phase, in which as good as no movement occurs in the examined region in which the most raw data lines can be read. There was a movement in the movement phase 52, as well as in the movement phase 53. If what is involved is an MR image of examination objects that are affected by the respiratory movement, the three movement phases can be by way of example the inhalation phase, the exhalation phase and an intermediate phase. With examinations in the region of the heart, phases such as the systole, the diastole and the interim contraction can be distinguished as different movement phases. In this embodiment all raw data lines of the raw data space are again recorded and allocated to a movement phase. The raw data lines can then be detected in which there was no movement, i.e. the movement phase in which the most raw data lines are present.

In the illustrated case the movement information has been divided into three different movement phases 51-53. Of course more or less than three movement phases can be distinguished.

An MR image can be determined with the use of Compressed Sensing Technology using the raw data lines that were recorded during the movement phase 53. This normally delivers good results for undersampling factors to a factor of 4. If Compressed Sensing Technology is to be used in order by way of example to reconstruct MR image in the movement phases 52 or 51 in which there are undersampling factors, such as greater than 6, the MR image calculated in the movement phase 53 is used as a reference image. This reference image is taken into account in the calculation of MR images in the movement phases 52 or 51 in which the raw data lines, which are each located outside of phases 52 or 51, are reconstructed. By use of the reference image of the movement phase 53, the fact is used in this connection that during a movement a large number of commonalities conventionally occur between an MR image in the movement phase 51 and the MR images in the movement phase 52 or 53, e.g. the contours of organs, the position of organ in the vicinity, etc. If the difference between these images is then produced in the movement phases 51, 52 or 53, an MR image with very little spatial information is obtained, so that reference is also made to a "sparse image". As a result of this requirement and the further requirement that there is a spatially randomly distributed undersampling of the raw data space, MR images can also be calculated using Compressed Sensing Technology for the movement phases 51 and 52. One solution in this connection is the use of Prior Image Constraint Compressed Sensing (PICCS) Technology with iterative image reconstruction. Technology of this kind operates up to undersampling factors of 20. In this method a cost function, which has a constancy term DF, is minimized, wherein the difference between the images and what is known as the sparsity transformation of the image to be calculated is minimized according to the following equation:

$$\tilde{x} = \arg\min_{x>0}\{DF(Ax_{M1}, y_{M1}) + \beta \cdot \|\psi(x_{M1} - x_{M0})\|_1 + (1-\beta) \cdot \|\psi(x_{M1})\|_1\}$$

where $DF(Ax,y) = (y-Ax)^T(y-Ax)$, $\|\psi(x)\|_1$=Sparsity Enforcing Term, M0, M1 are different movement phases of the examination object, x is the image to be reconstructed, y the measured raw data lines, $x_{M1}$ the image to be reconstructed in movement phase M1, $\beta$ a regularization term, A the transfer function of the MR system, and $x_{M0}$ is the reference image in the movement rest phase. The Sparsity Enforcing Term indicates how thinly occupied the image or difference image is.

Figure 6:
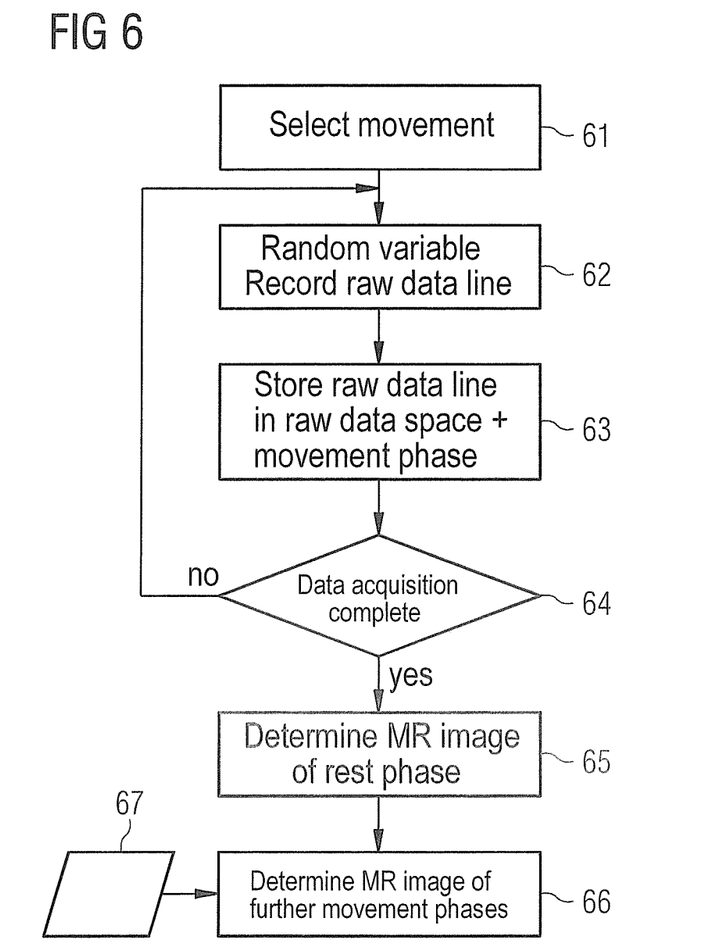
FIG. 6 is a flowchart of basic steps for calculating an MR image according to one aspect of the present invention.

FIG. 6 summarizes the steps with which MR images can be created in different movement phases with high undersampling factors, with the artifacts caused by the undersampling being nevertheless minimal.

In a step 61 the movement of the examination object or of the part of the examination object is detected from which an MR image is to be created. The detection of the movement by the movement detector 23 of FIG. 1 can occur by way of example through a breathing belt, ECG triggering or any other method that enables the movement of the examination object to be identified. As explained in connection with FIG. 5, the movement is also divided into different movement phases. In a step 62 the raw data lines are recorded in a temporally randomly distributed manner, as has been explained inter alia in connection with FIGS. 2-4. In a step 63 the recorded raw data line in the raw data space is stored with the associated movement information, so that it is known for each raw data line in which movement phase it was recorded. In a step 64 a check is made as to whether the data acquisition has finished, i.e. whether all desired raw data lines have been recorded. This can be the entire raw data space or just a portion thereof.

The reference image is created in a step 65. As has been explained in connection with FIG. 5, the reference image is the image in which the examination object was at rest and in which a large number of raw data lines were recorded. This reference image, shown schematically in FIG. 6 as reference image 67, is then taken into account as image information to determine MR images in the other movement phases (step 65), for example using the PICCS technology mentioned above. It is thereby possible to determine MR images in different movement phases, wherein the artifacts in the case of undersampled MR images in particular are minimized.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for acquiring magnetic resonance (MR) signals from an examination subject, comprising:
   operating an MR scanner to acquire MR signals from a subject in said MR scanner and, during acquisition of said MR signals, also acquiring movement information representing movement of the subject during the acquisition of said MR signals;
   providing said MR signals and said movement information to a processor, and grouping the movement information into different movement phases of the subject;
   from said processor, entering said MR signals into an electronic memory representing raw data space comprised of a plurality of raw data lines, in order to fill at least a predetermined portion of the raw data space with said MR signals, with said MR signals for the plurality of raw data lines being acquired according to a temporally randomly distributed sequence;
   in said processor, allocating each raw data line in said predetermined portion to one of said movement phases respectively, by identifying raw data lines in which said subject is in a rest phase of said movement, by identifying the movement phase comprising the most raw data lines, and reconstructing a reference image of said subject from the MR signals in said raw data lines in said rest phase, and thereby generating a data file comprising the raw data space filled with said MR signals acquired according to said temporally randomly distributed sequence; and
   making said data file available at an output of said processor in a form allowing reconstruction of an image of the subject from said MR signals in said data file.

2. A method as claimed in claim 1 comprising, in said processor, reconstructing another image of the subject from magnetic resonance signals in raw data lines that are not in said rest phase, and using said reference image.

3. A method as claimed in claim 2 comprising reconstructing said another image of the subject by executing an iterative reconstruction algorithm in said processor, in which a cost function is minimized.

4. A method as claimed in claim 3 wherein said cost function includes a Sparsity Enforcing Term.

5. A method as claimed in claim 1 comprising entering said MR signals into the raw data space according to said temporally randomly distributed sequence in a peripheral region of the raw data space outside of a predetermined central region of the raw data space.

6. A method as claimed in claim 1 wherein said electronic memory is organized with said raw data space as a three-dimensional raw data space comprising a first direction, and a second direction that is perpendicular to said first direction, and comprising generating said temporally randomly distributed sequence in said processor with said raw data lines being temporally randomly filled with MR signals along said first direction and with raw data lines being temporally randomly filled with said MR signals also along said second direction.

7. A method as claimed in claim 6 comprising operating said MR scanner to acquire said MR signals by activating a readout gradient, along a readout direction, with gradient coils of said MR scanner, and acquiring said MR signals during said readout gradient, and wherein said readout gradient corresponds to a third direction of the raw data space that is perpendicular to said first direction and to said second direction.

8. A method as claimed in claim 1 wherein said raw data lines are radial raw data lines each proceeding through a center of the raw data space, and generating said temporally randomly distributed sequence in said processor to cause said MR signals to be temporally randomly distributed along said radial raw data lines.

9. A method for acquiring magnetic resonance (MR) signals from an examination subject, comprising:
    operating said MR scanner to acquire MR signals from a subject in said MR scanner by activating a phase encoding gradient with gradient coils of said MR scanner that encodes said MR signals in a phase encoding direction and, during acquisition of said MR signals, also acquiring movement information representing movement of the subject during the acquisition of said MR signals;
    providing said MR signals and said movement information to a processor, and grouping the movement information into different movement phases of the subject;
    generating a temporally randomly distributed sequence in said processor;
    from said processor, entering said MR signals into an electronic memory representing raw data space organized as a two-dimensional Cartesian raw data space comprised of a plurality of raw data lines, in order to fill at least a predetermined portion of the raw data space with said MR signals, with said MR signals for the plurality of raw data lines being acquired according to said temporally randomly distributed sequence with said raw data lines being filled in said phase encoding direction;
    in said processor, allocating each raw data line in said predetermined portion to one of said movement phases respectively, thereby generating a data file comprising the raw data space filled with said MR signals acquired according to said temporally randomly distributed sequence; and
    making said data file available at an output of said processor in a form allowing reconstruction of an image of the subject from said MR signals in said data file.

10. A magnetic resonance (MR) apparatus comprising:
    an MR scanner;
    a control computer configured to operate MR scanner to acquire MR signals from a subject in said MR scanner and, during acquisition of said MR signals, also to acquire movement information representing movement of the subject during the acquisition of said MR signals;
    said control computer being configured to group the movement information into different movement phases of the subject;
    an electronic memory representing raw data space comprised of a plurality of raw data lines;
    said control computer being configured to enter said MR signals into said electronic memory in order to fill at least a predetermined portion of the raw data space with said MR signals, with said MR signals for the plurality of raw data lines being acquired according to a temporally randomly distributed sequence;
    said control computer being configured to allocate each raw data line in said predetermined portion to one of said movement phases respectively, so as to thereby generate a data file comprising the raw data space filled with said MR signals according to said temporally randomly distributed sequence;
    said control computer being configured to identify raw data lines in which said subject is in a rest phase of said movement, by identifying the movement phase comprising the most raw data lines, and to reconstruct a reference image of said subject from the MR signals in said raw data lines in said rest phase; and
    said control computer being configured to make said data file available at an output of said control computer in a form allowing reconstruction of an image of the subject from said MR signals in said data file.

11. An apparatus as claimed in claim 10 wherein said control computer is configured to enter said MR signals into the raw data space according to said temporally randomly distributed sequence in a peripheral region of the raw data space outside of a predetermined central region of the raw data space.

12. A magnetic resonance (MR) apparatus comprising:
    an MR scanner;
    a control computer configured to operate MR scanner to acquire MR signals from a subject in said MR scanner by activating a phase encoding gradient with gradient coils of said MR scanner that encodes said MR signals in a phase encoding direction and, during acquisition of said MR signals, also to acquire movement information representing movement of the subject during the acquisition of said MR signals;
    said control computer being configured to group the movement information into different movement phases of the subject;
    an electronic memory representing raw data space organized as a two-dimensional Cartesian raw data space comprised of a plurality of raw data lines;
    said control computer being configured to generate a temporally randomly distributed sequence;
    said control computer being configured to enter said MR signals into said electronic memory in order to fill at least a predetermined portion of the raw data space with said MR signals, with said MR signals for the plurality of raw data lines being acquired according to said temporally randomly distributed sequence with said raw data lines being filled in said phase encoding direction;
    said control computer being configured to allocate each raw data line in said predetermined portion to one of said movement phases respectively, so as to thereby generate a data file comprising the raw data space filled with said MR signals according to said temporally randomly distributed sequence; and said control computer being configured to make said data file available at an output of said control computer in a form allowing reconstruction of an image of the subject from said MR signals in said data file.

\* \* \* \* \*